United States Patent
Kalus (10) Patent No.: US 9,114,003 B2
(45) Date of Patent: Aug. 25, 2015

(54) SURGICAL METHODS FOR BREAST IMPLANTS

(71) Applicant: R&D Concepts, LLC, Charleston, SC (US)

(72) Inventor: Ram Kalus, Charleston, SC (US)

(73) Assignee: R & D Concepts, LLC, Charleston, SC (US)

( * ) Notice: Subject to any disclaimer, the term of this patent is extended or adjusted under 35 U.S.C. 154(b) by 0 days.

(21) Appl. No.: 13/833,725

(22) Filed: Mar. 15, 2013

(65) Prior Publication Data
US 2014/0081397 A1 Mar. 20, 2014

Related U.S. Application Data

(60) Provisional application No. 61/702,912, filed on Sep. 19, 2012.

(51) Int. Cl.
*A61F 2/12* (2006.01)
*A61B 19/00* (2006.01)

(52) U.S. Cl.
CPC . *A61F 2/12* (2013.01); *A61B 19/46* (2013.01); *A61B 2019/461* (2013.01); *A61F 2240/005* (2013.01)

(58) Field of Classification Search
CPC .......................................................... A61F 2/12
USPC ............................................................. 623/8
See application file for complete search history.

(56) References Cited

U.S. PATENT DOCUMENTS

| | | | | |
|---|---|---|---|---|
| 6,055,989 A | * | 5/2000 | Rehnke | 128/898 |
| 2004/0059413 A1 | * | 3/2004 | Argento | 623/2.11 |
| 2005/0021142 A1 | * | 1/2005 | Ganz et al. | 623/16.11 |
| 2009/0149953 A1 | | 6/2009 | Schuessler et al. | |
| 2013/0018393 A1 | * | 1/2013 | Bengtson | 606/144 |

FOREIGN PATENT DOCUMENTS

FR 2 859 098 3/2005

OTHER PUBLICATIONS

International Search Report and Written Opinion of the International Searching Authority for corresponding International Application No. PCT/US2013/060520 mailed Jan. 3, 2014.

* cited by examiner

*Primary Examiner* — Randy Shay
(74) *Attorney, Agent, or Firm* — Womble Carlyle Sandridge & Rice, LLP (57) ABSTRACT

Surgical tools, kits, and methods for breast implants are provided. One surgical tool is a rigid or semi-rigid form that matches the size and shape of a corresponding breast implant. The form may be employed to determine skin tension when inserted into a breast. The form may also be employed to mark a fixation suture line for attachment between an acellular dermal matrix and the chest wall of a patient in some instances. However, in other instances a breast implant template surgical tool may be employed to mark one or more fixation suture lines. The breast implant template may be thin and flexible, and define a perimeter matching the size and shape of a footprint of a corresponding breast implant. Marking around the perimeter of the form or the breast implant template allows for convenient selection of fixation suture lines which may result in desirable overall breast symmetry.

3 Claims, 11 Drawing Sheets

SURGICAL METHODS FOR BREAST IMPLANTS

TECHNICAL FIELD

The present disclosure relates generally to intra-operative surgical tools or devices, and more particularly to surgical tools or devices, kits, and methods for determining proper breast implant sizes which may, for example, be employed in immediate, direct-to-implant ("DTI") breast reconstruction following mastectomy.

BACKGROUND

Few specific intra-operative surgical tools or devices have been developed for determining the proper size for breast implants which may be, for example, used in the setting of immediate breast reconstruction. Some of these methods and surgical tools have been developed for office based assessments both for reconstructive and cosmetic enhancement purposes. Additional methods and surgical tools and devices have been developed for intra-operative use in reconstructive patients specifically.

By way of example, one embodiment of a breast reconstructive procedure employs a tissue expander to create a pocket underneath the skin (subcutaneous) and chest muscle (sub-pectoral) of a patient. The tissue expander may be expanded over a period of several weeks to months to create a pocket or space having a size sufficient to accept an implant. Thereafter, in a second surgical procedure, a breast implant may be inserted into the pocket created by the tissue expander, and in place thereof.

More recently, a "one-step" or "direct-to-implant" ("DTI") breast reconstructive procedure has been developed. DTI procedures may be desirable in that they may involve a single procedure wherein the mastectomy and reconstruction are both performed and completed under one anesthetic. In this regard, the insertion of an acellular dermal matrix ("ADM") material may be employed to assist in forming a pocket and support for the implant, thus providing a first layer of soft tissue coverage over the implant, the second more superficial layer being the skin and subcutaneous tissue which constitutes the mastectomy skin flaps.

However, DTI breast reconstruction is dependent on sufficient skin laxity to allow for safe wound closure without undue tension that could compromise healing and jeopardize the reconstruction. Therefore, in the setting of DTI breast reconstruction, whether unilateral or bilateral, the two critical steps are the proper sizing and positioning of the breast implant(s), and the proper determination of the suture line for insetting of the ADM. Accordingly, improved apparatuses, tools, devices, systems, and methods for determination of optimal breast implant size and proper suture line insetting of the ADM may be desirable.

SUMMARY

As described herein, surgical tools or devices are provided that may improve the safety and predictability of breast reconstruction procedures, such as direct to implant procedures employing an ADM. A rigid or semi-rigid three dimensional form may be employed to assess the tension on skin when the rigid or semi-rigid form is inserted into the post-mastectomy breast pocket. The form may be designed to mimic the exact dimensions of the predicted or desired breast implant and may be used to define the three-dimensional shape that matches the size and shape of the corresponding implant. Once it has been determined that the given implant size is suitable and "fits" into the mastectomy pocket without undue tension, the surgeon may mark around the perimeter of the form to determine the precise location of the fixation suture line for the ADM. Alternatively, a two-dimensional breast implant template that is flexible and thin may be employed to mark the location of the fixation suture line if, for example, it is clinically apparent that there is adequate skin coverage to safely accept the selected implant. The breast implant template may similarly be used to define a perimeter that matches the perimeter of the corresponding breast implant in both size and shape. The three-dimensional forms and the two-dimensional templates may be provided in various sizes and shapes matching the sizes and shapes of existing breast implants of major manufacturers, and my be color coded for simplicity of use.

In one aspect a surgical tool is provided. The surgical tool may include a breast implant template comprising a sheet of a flexible material defining a perimeter with a shape and one or more dimensions corresponding to and configured to substantially match a shape and one or more dimensions of a perimeter of a breast implant. The perimeter of the sheet of the flexible material may be configured to determine a fixation suture line for attaching an acellular dermal matrix to a chest wall of a patient to prepare a breast thereof for receiving the breast implant.

In some embodiments the surgical tool may be configured to be reusable or disposable. Further, the material may comprise a silicone rubber. The shape of the perimeter of the sheet of the flexible material may be a circle or an anatomic shape. The perimeter of the sheet of the flexible material may define a diameter from about 10.0 centimeters to about 16.0 centimeters.

In an additional aspect a breast implant kit is provided. The breast implant kit may include a breast implant defining a perimeter with a shape and one or more dimensions. Further, the breast implant kit may include a breast implant template comprising a sheet of a flexible material defining a perimeter with a shape and one or more dimensions corresponding to and configured to substantially match the shape and the dimensions of the perimeter of the breast implant. The perimeter of the sheet of the flexible material may be configured to determine a fixation suture line for attaching an acellular dermal matrix to a chest wall of a patient to prepare a breast thereof for receiving the breast implant.

In some embodiments the breast implant template may be configured to be reusable or disposable. The material of the breast implant template may comprise a silicone rubber. The breast implant kit may additionally include the acellular dermal matrix. The shape of the perimeter of the sheet of the material and the shape of the perimeter of the breast implant may be a circle or an anatomic shape. The perimeter of the sheet of the material and the breast implant may each define a diameter from about 10.0 centimeters to about 16.0 centimeters.

In a further aspect a surgical method is provided. The surgical method may include providing an acellular dermal matrix, suturing the acellular dermal matrix to a pectoralis muscle of a patient, providing a breast implant defining a perimeter with a shape and one or more dimensions, providing a breast implant template comprising a sheet of a flexible material defining a perimeter with a shape and one or more dimensions substantially matching the shape and the dimensions of the perimeter of the breast implant, inserting the breast implant template under the pectoralis muscle, selecting a position of a fixation suture line on a chest wall of the patient based on a position of the perimeter of the breast implant template, suturing the acellular dermal matrix to the chest wall along the fixation suture line, and inserting the breast implant between the pectoralis muscle and the acellular dermal matrix.

In some embodiments selecting the position of the fixation suture line may include marking the chest wall. The method may additionally include selecting the breast implant template with the shape and the dimensions substantially matching the shape and the dimensions of the perimeter of the breast implant from a plurality of breast implant templates defining at least one of a plurality of shapes and a plurality of sizes.

In an additional aspect a surgical tool is provided. The surgical tool may include a three-dimensional form comprising a form-stable material defining a shape and one or more dimensions corresponding to and configured to substantially match a shape and one or more dimensions of a breast implant. The form may be configured for temporary insertion under a pectoralis muscle of a patient to determine a skin tension that would be associated with insertion of the breast implant substantially matching the shape and the dimensions of the form.

In some embodiments the form may be configured to be reusable or disposable. The form may define a volume that is substantially equal to a volume of the breast implant. The shape of the form may be hemispherical. Further, the form may define a diameter from about 10.0 centimeters to about 16.0 centimeters.

In another aspect a breast implant kit is provided. The breast implant kit may include a breast implant defining a shape and one or more dimensions. The breast implant kit may additionally include a form comprising a form-stable material defining a shape and one or more dimensions corresponding to and configured to substantially match the shape and the dimensions of the breast implant. The form may be configured for temporary insertion under a pectoralis muscle of a patient to determine a skin tension that would be associated with insertion of the breast implant substantially matching the shape and the dimensions of the form.

In some embodiments the form may be configured to be reusable or disposable. The form may define a volume that is substantially equal to a volume of the breast implant. The shape of the form may be hemispherical. The form may define a diameter from about 10.0 centimeters to about 16.0 centimeters. The breast implant may further include an acellular dermal matrix.

In a further aspect a surgical method is provided. The surgical method may include providing a plurality of breast implants respectively defining a perimeter with a shape and one or more dimensions, providing a plurality of forms comprising a form-stable material defining a shape and one or more dimensions respectively configured to substantially match the shape and the dimensions of the breast implants, inserting one of the forms under a pectoralis muscle of a patient, determining if the shape and the dimensions of the one of the forms that has been inserted are acceptable, removing the one of the forms from under the pectoralis muscle, selecting one of the breast implants matching the shape and the dimensions of the one of the forms that was inserted in an instance in which the shape and the dimensions of the one of the forms that has been inserted are acceptable, and inserting the one of the breast implants under the pectoralis muscle.

In some embodiments determining if the shape and the dimensions of the one of the forms that has been inserted are acceptable may include determining if a skin tension around the one of the forms that has been inserted is acceptable. The method may additionally include providing an acellular dermal matrix, suturing the acellular dermal matrix to the pectoralis muscle, and suturing the acellular dermal matrix to the chest wall.

Other apparatuses, systems, methods, features and advantages of the disclosure will be or will become apparent to one with skill in the art upon examination of the following figures and detailed description. It is intended that all such additional systems, methods, features and advantages be included within this description, be within the scope of the disclosure, and be protected by the accompanying claims.

BRIEF DESCRIPTION OF THE DRAWINGS

The included drawings are for illustrative purposes and serve only to provide examples of possible structures and arrangements for the disclosed assemblies, methods, and systems. These drawings in no way limit any changes in form and detail that may be made to the disclosure by one skilled in the art without departing from the spirit and scope of the disclosure.

DETAILED DESCRIPTION

Example applications of apparatuses, systems, and methods according to the present disclosure are described in this section. These examples are being provided solely to add context and aid in the understanding of the disclosure. It will thus be apparent to one skilled in the art that the present disclosure may be practiced without some or all of these specific details. In other instances, well known process steps have not been described in detail in order to avoid unnecessarily obscuring the present disclosure. Other applications are possible, such that the following examples should not be taken as limiting.

Figure 1:
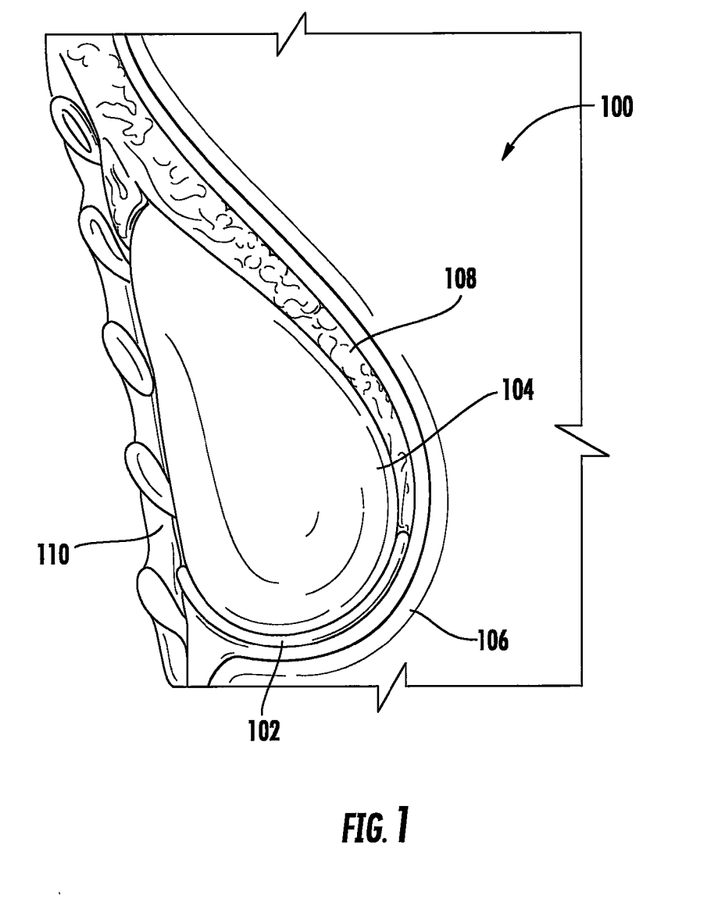
FIG. 1 illustrates a cross-sectional view through a breast that has been reconstructed using a breast implant and an acellular dermal matrix.

Direct-to-implant ("DTI") breast reconstruction procedures may be employed to reconstruct a breast in as few as one surgical procedure in some embodiments. In this regard, FIG. 1 illustrates a cross-sectional view through a breast 100 which has been reconstructed using a direct-to-implant procedure. As illustrated, an acellular dermal matrix ("ADM") 102 is positioned in the breast 100 such that it may support an implant 104 and provide a layer of material between the implant and the mastectomy skin flap 106. In this regard, the acellular dermal matrix 102 assists in forming a pocket between the pectoralis muscle 108 and the chest wall 110 into which the implant 104 may be received without requiring significant expansion of the surrounding tissue, effectively extending the reach of the pectoralis muscle such that a complete inner layer surrounds and encompasses an implant received in the breast 100. The ADM 102 effectively acts as a hammock to support the implant 100 in the lower pole of the reconstructed breast.

However, the selection of the size of the implant 104 is critical. In this regard, the skin flap 106 may be of adequate supply such that the breast skin may be closed without imparting undue tension thereon. Excessive tension on the skin flap 106 may compromise the blood supply thereto and potentially lead to wound healing complications or even a failed breast reconstruction.

Figure 2:
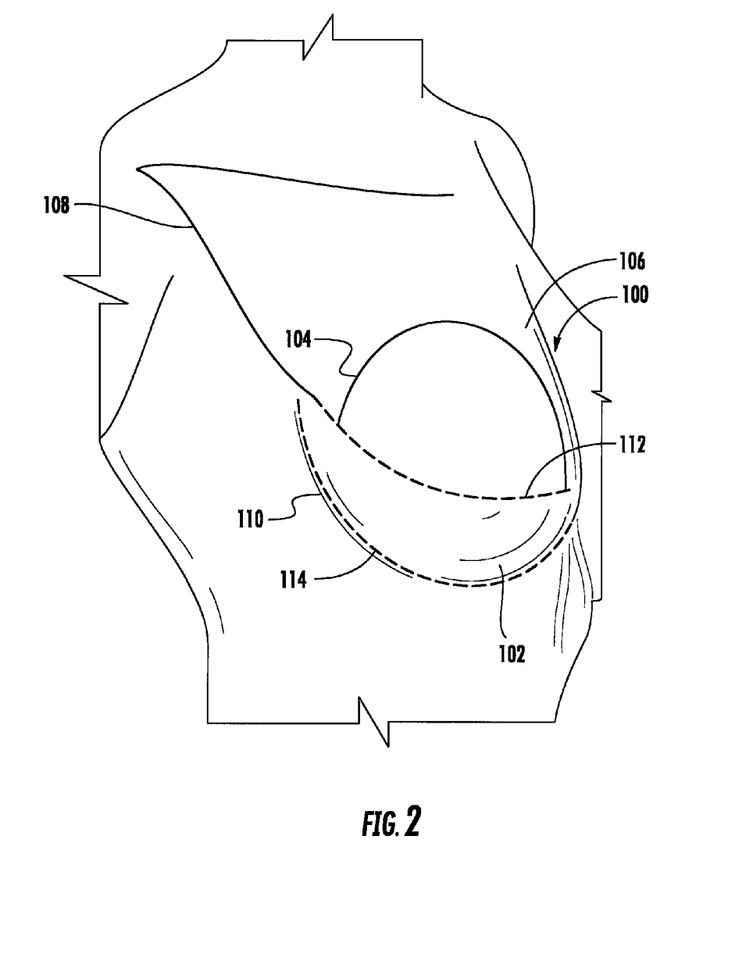
FIG. 2 illustrates a modified perspective view of the breast of FIG. 1.

As illustrated in FIG. 2, the acellular dermal matrix 102 may be sutured to the pectoralis muscle 108 along a first fixation suture line 112. Further, the acellular dermal matrix 102 may be sutured to the chest wall 110 along a second fixation suture line 114. The placement of the fixation suture lines 112, 114 determine the location of the inframammary fold, medial mammary fold, and lateral mammary fold. The position of the inframammary, medial, and lateral folds may affect the cosmetic appearance of the breast 100. In this regard, it may be important to provide each breast with matching symmetrical inframammary and lateral folds to result in symmetrical breasts. This is equally true in the setting of a unilateral breast reconstruction to achieve symmetry with the opposite breast, as well as in the setting of bilateral breast reconstructions to achieve symmetry between each of the breast reconstructions.

Accordingly, existing embodiments of DTI breast reconstructive procedures may suffer from the two challenges noted above. Namely, the size of the implant must be properly determined in advance of inserting the breast implant to ensure that the surrounding tissue is not subjected to excessive tension. Further, the location of the fixation suture lines must be properly selected to ensure proper breast implant position and symmetry.

With respect to the issue of ensuring that an implant is properly sized for the patient, implant sizers presently exist. The implant sizers are sterile, reusable, and configured to be identical to the corresponding breast implants. In this regard, the implant sizers may comprise silicone, which makes the implant sizers soft and pliable like the actual breast implants. However, Applicant has determined that as a result of the implant sizers being soft and pliable, they may be difficult to work with. In particular, the implant sizers may move around and shift position when inserted in the breast, making it difficult for the surgeon performing the operation to assess the resulting tension on the acellular dermal matrix, skin, muscle, and other tissue, and present further difficulty in acting as a template or stencil by which to determine the fixation suture line for the ADM.

Figure 3:
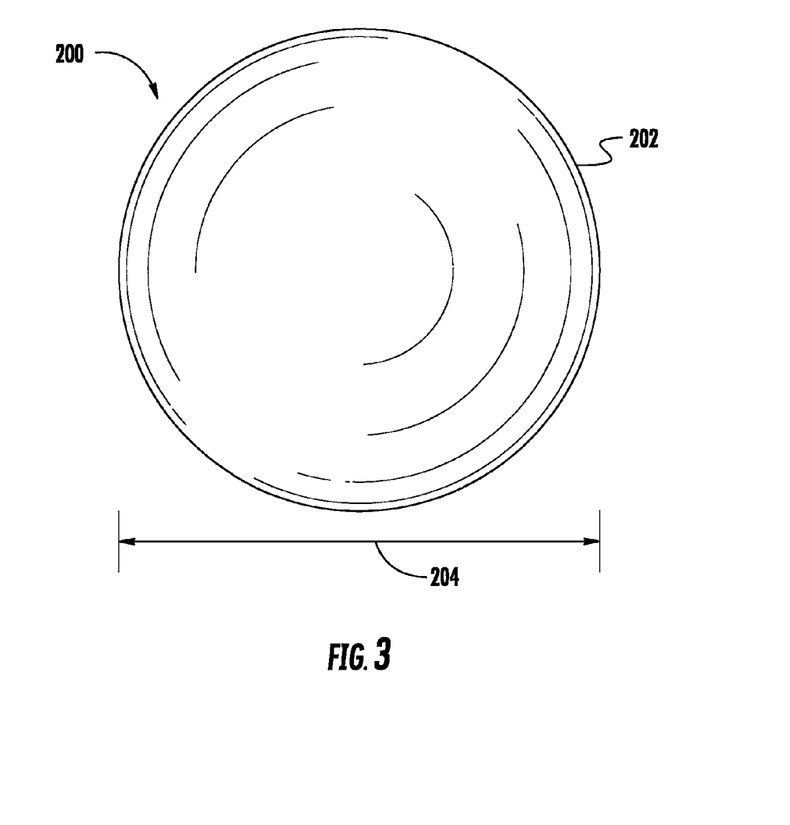
FIG. 3 illustrates a top view of a three-dimensional form according to an embodiment of the present disclosure.
Figure 4:
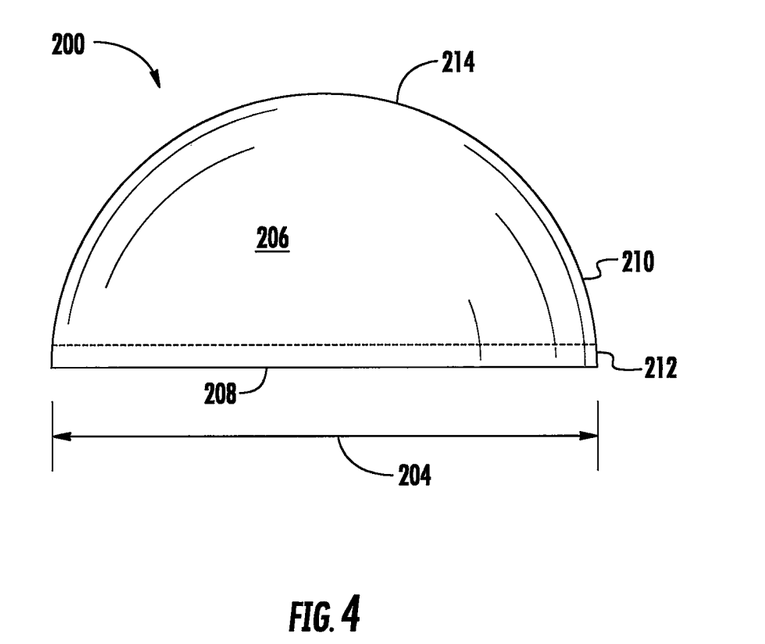
FIG. 4 illustrates a side view of the form of FIG. 3.

Accordingly, Applicant herein provides embodiments of an improved three-dimensional ("3-D") sizer or form, which may be usable as a surgical device or tool. FIG. 3 illustrates an overhead view of the form 200. The form 200 may define a shape and one or more dimensions configured to substantially match a shape and one or more dimensions of a breast implant. In this regard, as illustrated in FIG. 3, a perimeter 202 of the form 200 may be circular, as illustrated in FIG. 4. Thus, by way of example, the overall shape of the form 200 may be hemispherical, in order to substantially match the shape of a breast implant. Alternatively the form may be oval or anatomically shaped to mimic the form stable or anatomic breast implant devices more recently introduced to the market.

The form 200 may define a diameter 204 that corresponds to a diameter of a matching breast implant. In this regard, breast implants are presently sold in diameters ranging from about 10 centimeters to about 16.0 centimeters. Accordingly, the form 200 may be provided in the same shapes with matching diameters and other dimensions such that the 3-D form defines a volume and dimensions that are substantially equal to a volume and dimensions of the corresponding breast implant.

In order to avoid the issues noted above with respect to existing embodiments of breast implant sizers shifting position and otherwise being difficult to work with, the form 200 provided herein may comprise a form-stable material. Form-stable, as used herein, refers to a material that is either substantially rigid or semi-rigid. Accordingly, the material substantially retains the same shape regardless of the orientation thereof. In contrast, breast implants may not be form-stable. Thus, when reoriented, the shape of the breast implant may change. For example, the form 200 may comprise form-stable materials such as a plastic material, a rubber material, a metal material, glass, foam, or any other embodiment of material configured to provide the form 200 with self-support, form stability, and ease of insertion even through a small skin sparing mastectomy incision.

The form 200 may be configured with a smooth, low friction outer surface 206 that allows the form 200 to contact tissue without traumatizing the tissue. In one embodiment the entirety of the outer surface 206 of the form 200 may be consistent in both material composition and texture (or lack thereof). For example, in some embodiments the form 200 may be integrally formed from a single piece of material and define a smooth outer surface. Further, in some embodiments the material of the form 200 may be selected to define a substantially low coefficient of friction configured to minimize tissue damage. For example, the form may comprise a silicone rubber.

However, in other embodiments the outer surface 206 of the form 200 may define properties that differ depending on a location thereon. For example, a bottom surface 208 of the form 200 may define a greater coefficient of friction than a remainder of the outer surface. Accordingly, the bottom surface 208 may frictionally engage the chest wall surface against which the bottom surface of the form 208 is placed during use.

In some embodiments the bottom surface 208 may define a pattern or texture (e.g., a diamond-shaped pattern) in order to increase the coefficient of friction thereof. Alternatively or additionally, the bottom surface 208 may comprise a different material than a remainder of the form 200. For example, as illustrated in FIG. 4, an upper portion 210 of the form 200 may comprise a first material, whereas a bottom portion 212 of the form may define a second material. By way of further example, the bottom portion 212 of the form 200 may comprise a plastic material whereas the top portion 210 of the form may comprise a rubber material, wherein the rubber material defines a relatively lower coefficient of friction.

However, various other combinations of materials and/or textures may be employed to configure a top surface 214 of the form 200 to define a relatively lower coefficient of friction with respect to surrounding tissue as compared to the bottom surface 208. In an additional embodiment a friction enhancing coating may be applied to the bottom surface 208 of the form 200 and/or a friction reducing coating or fluid may be applied to the top surface 214 of the form. Accordingly, differing coefficients of friction at the top surface 214 and the bottom surface 208 of the form 200 may be achieved via one or more of the above-described implementations. In this regard, frictional engagement of the bottom surface 208 of the form 200 with the chest wall may be desirable in order to ensure that the form remains in a desired position during tracing of the perimeter thereof during use, as will be described below. Further, minimization of the frictional engagement of the top surface 214 of the form 200 with the pectoralis muscle may be desirable in order to prevent damage thereto.

The form 200 may also be formed from two or more materials for other purposes. For example, the bottom portion 212 of the form 200 may comprise a material that is substantially rigid and provide a stable material for tracing a perimeter around, as discussed below. Further, the top portion 210 of the form may comprise a compressible material, such as foam or rubber that facilitates insertion into the breast cavity by allowing for compression of the form 200 to smaller dimensions during insertion and removal therefrom. Thereby, the top portion 212 of the form may be manipulated to facilitate insertion and removal and yet define a form-stable shape while positioned in the breast cavity. In another embodiment the form 200 may be configured to fold such that entry into, and removal from, the breast cavity may be facilitated.

As noted above, in some embodiments the form may be designed to mimic an oval or anatomical shape. In this embodiment the form may define one or more orientation marks on the outer surface thereof. For example, a major axis reference line may be marked on the outer surface of the form and/or markers may indicate top and bottom portions thereof such that a surgeon may align the reference line with a vertical orientation during use to ensure proper orientation of the form.

In an additional embodiment the form may be hollow. For example, the form may be partially or fully open at the back surface in some embodiments. Thus, the form may define a bowl shape with a concave back surface and a convex top surface. Use of a hollow form with an open back surface may allow the form to mimic the size and shape of a breast implant and allow a surgeon to trace around the perimeter thereof, as described below, while limiting engagement of the form with the chest wall to the perimeter edge of the form. Accordingly, the peripheral edge of the form may engage the chest wall while the remainder of the form may be out of contact with the chest wall. Thereby, variations in the height of the chest wall may not affect the ability of the form to rest in a stable position thereon. Further, use of a bowl shape and an elastic material such as silicone rubber may allow the form to be folded into a "taco shape" during insertion and removal, which may facilitate insertion and removal thereof from the breast cavity.

In use, the form 200 may be temporarily inserted under the mastectomy skin flaps or under the pre-elevated pectoralis muscle of a patient to determine the tension on the acellular dermal matrix, the skin flaps, and/or the pectoralis muscle that would be associated with insertion of a breast implant substantially matching the shape and the dimensions of the form. If the skin tension or other resulting characteristic of the breast upon insertion of the form 200 is determined by the surgeon to be undesirable (e.g., when the skin tension is too high), an alternately sized or alternately shaped form may be inserted into the breast. This process may be repeated as necessary until a form 200 that results in an ideal breast configuration is found (e.g., with sufficiently low or otherwise acceptable skin tension). Thereby, a breast implant corresponding in size and shape to the selected form 200, that properly fits in the breast, may be implanted in the breast in place of the form.

Since the form 200 is form-stable (e.g., rigid or semi-rigid), insertion and removal thereof from the breast may be expedited as compared to pliable breast implant sizers. Given that this process occurs during the surgical operation, reduction in the time associated with selection of the breast implant may be of great importance to the health and safety of the patient. In addition to the potential for reduction of time associated with selection of the breast implant, the form 200 may also provide benefits in terms of potentially eliminating the need for use of temporary sutures between the acellular dermal matrix and the chest wall. In this regard, due to the form 200 being defined by a substantially rigid or semi-rigid material, the form may retain the desired hemispherical shape when inserted into the breast. Thus, skin tension may be assessed without first employing the acellular dermal matrix to form a pocket, which may be required when employing a pliable implant sizer.

In one embodiment the form 200 may also be employed to select and mark the location of the suture lines employed to inset the ADM and secure the final breast implant in place (e.g. the fixation suture line between the ADM and the chest wall and/or the fixation suture line between the ADM and the pectoralis muscle). In this regard the surgeon may trace around the perimeter of the form to locate the fixation suture line(s). Note that presently the fixation suture line between the acellular dermal matrix and the chest wall may be determined without the use of a surgical tool (i.e., by visually determining the placement of the fixation suture line). Alternatively, the surgeon may employ a pliable implant sizer to mark the location of the fixation suture line between the acellular dermal matrix and the chest wall. However, due to the flexible nature of the pliable implant sizer, which may be silicone gel filled, saline-filled, or air-filled, marking the suture line may be difficult, since the pliable implant size may move or shift position. Accordingly, the rigid or semi-rigid form 200 provided herein may facilitate selection and marking of the fixation suture line(s).

After use of the form 200, the form may be disposed of. Alternatively, the form 200 may be sterilized and reused. In this regard, the form 200 may define a material such as surgical steel configured to withstand the high temperatures and/or chemical exposure associated with sterilization (e.g. in an autoclave), in some embodiments.

In some embodiments the form 200 may be provided as part of a breast implant kit comprising the form and a breast implant and/or an acellular dermal matrix. The form 200 may also be provided in various sizes and shapes that match the sizes and shapes of a variety of breast implants. Thereby, the forms 200 may be configured to precisely match the size and shape of the breast implants, as described above.

Figure 5:
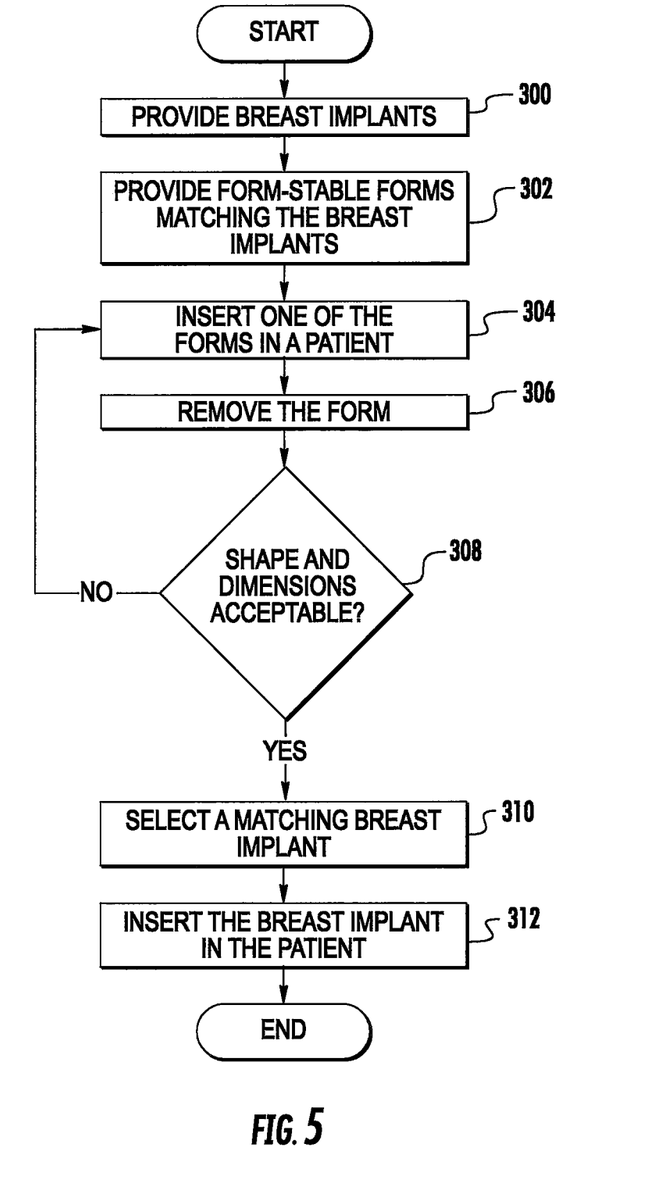
FIG. 5 illustrates a schematic diagram of a surgical method employing a form according to an example embodiment of the present disclosure.

A related surgical method is also provided. As illustrated in FIG. 4, the method may comprise providing a plurality of breast implants respectively defining a perimeter with a shape and one or more dimensions at operation 300 and providing a plurality of forms comprising a form-stable (e.g., rigid or semi-rigid) material defining a shape and one or more dimensions respectively configured to substantially match the shape and the dimensions of the breast implants at operation 302. The method may also include inserting one of the forms under a pectoralis muscle of a patient at operation 304. Further, the method may include removing the one of the forms from under the pectoralis muscle at operation 306. Additionally, the method may include determining if the shape and the dimensions of the one of the forms that has been inserted are acceptable at operation 308. Note that although the determination of whether or not the shape and dimensions of the form at operation 308 may be conducted prior to removing the form at operation 306, the method may not differ until after the form is removed at operation 306.

In this regard, if the form is not determined to be acceptable at operation 308, the method may return to operation 304, at which a different one of the forms may be inserted. However, in an instance in which the shape and the dimensions of the one of the forms that has been inserted are determined to be acceptable at operation 308, the method may proceed to selecting one of the breast implants matching the shape and the dimensions of the one of the forms that was inserted at operation 310. Further, the method may include inserting the one of the breast implants under the pectoralis muscle at operation 312.

The method may additionally include providing an acellular dermal matrix, (ADM), suturing the ADM to the pectoralis muscle, and suturing the ADM to the chest wall. In some embodiments determining if the shape and the dimensions of the one of the forms that has been inserted are acceptable at operation 308 may comprise determining if a skin tension around the one of the forms that has been inserted is acceptable. In other embodiments tension on the ADM, pectoralis muscle, and/or other surrounding tissue (e.g., the mastectomy skin flaps) may be determined at operation 308.

Additionally the method may include selecting a position of a fixation suture line on a chest wall of the patient based on a position of the perimeter of the form. Selecting the position of a fixation suture line may comprise marking the chest wall. However, in other embodiments the form may not be employed to select the position of the fixation suture line on the chest wall.

Figure 6:
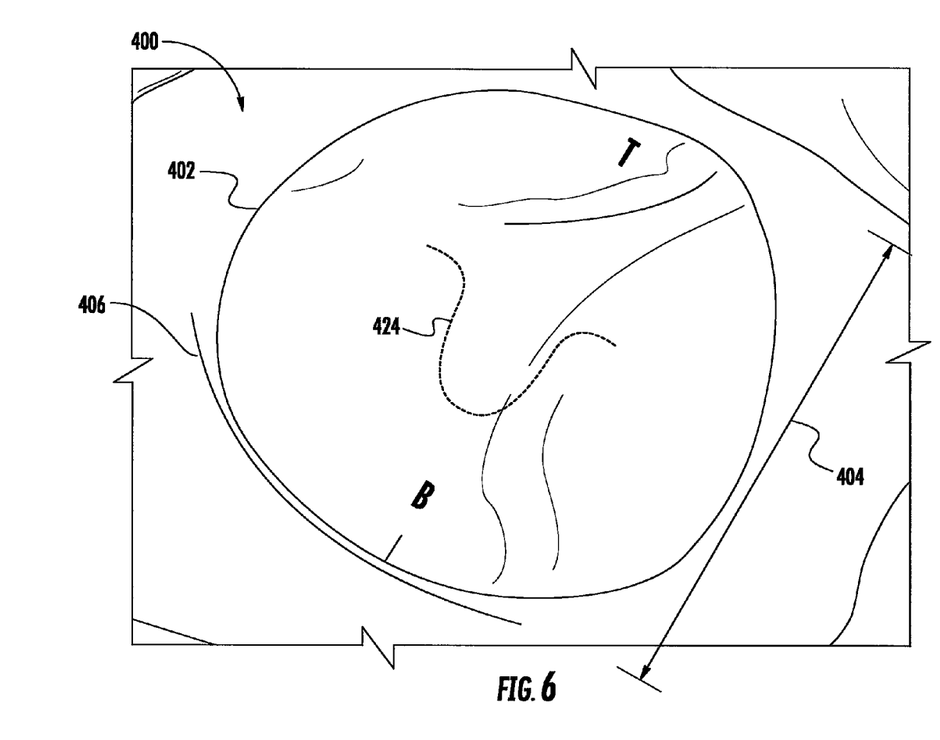
FIG. 6 illustrates a perspective view of a two-dimensional breast implant template lying on top of a mastectomy site according to an example embodiment of the present disclosure.

In this regard, FIG. 6 illustrates an embodiment of a two-dimensional (2-D) breast implant template 400 surgical tool. Two-dimensional, as used herein, refers to the generally flat, planar, shape and configuration of the template 400 in which the template defines a substantially constant, and relatively, thin thickness (e.g., about 5 mm or less) between opposing top and bottom substantially planar surfaces. The breast implant template 400 may comprise a sheet of a flexible material. The breast implant template 400 may be formed from various embodiments of flexible materials. For example, the breast implant template 400 may comprise a silicone rubber material. Thus, in some embodiments the breast implant template 400 may be folding during insertion into, and/or removal from the breast cavity. Additionally, the template 400 may be configured with a top surface defining a lower coefficient of friction than a bottom surface as described above with respect to the form 200. For example, the bottom surface may be textured or define a differing material or coating as compared to the top surface in the manners and for the reasons described above. Further, in some embodiments the breast implant template 400 may be configured to be disposable, whereas in other embodiments the breast implant template may be configured to be reusable (e.g., through sterilization thereof in an autoclave).

The sheet of flexible material may define a perimeter 402 with a shape and one or more dimensions configured to substantially match a shape and one or more dimensions of a perimeter of a breast implant. In this regard, the breast implant 2-D template 400 may define a circle with a diameter 404 that corresponds to a diameter of a matching breast implant. Breast implants are presently sold in diameters from about 10.0 centimeters to about 16.0 centimeters. Accordingly, the breast implant template 400 may be provided in the same shapes with matching diameters and other dimensions such that the breast implant template defines an area that substantially matches a footprint of a corresponding breast implant.

The perimeter 402 of the sheet of the flexible material is configured to locate a fixation suture line for attaching an ADM to the chest wall of a patient. Note that although the above-described form 200 may be employed to mark one or more fixation suture lines, the 2-D breast implant template 400 provided herein may alternatively be employed for this purpose. For example, use of the breast implant template 400, which may be thin and substantially define a two-dimensional shape, may allow for easier marking of suture lines by occupying less space in the cavity in the breast than the three-dimensional shape of the form 200. Thus, in some embodiments the breast implant template 400 may be inserted into the breast after the proper size of a breast implant is determined using the form 200, and the breast implant 2-D template may then be employed to select the location of one or more fixation suture lines. Alternatively, in some instances patients may have breasts which define an ample quantity of skin and soft tissue that clearly allows for use of a particular desired size of a breast implant. In these instances use of the 3-D form 200 may be unnecessary, and hence the breast implant 2-D template 400 may be employed to select and mark one or more fixation suture lines. Accordingly, the breast implant templates 400 may be employed in various circumstances.

Figure 7:
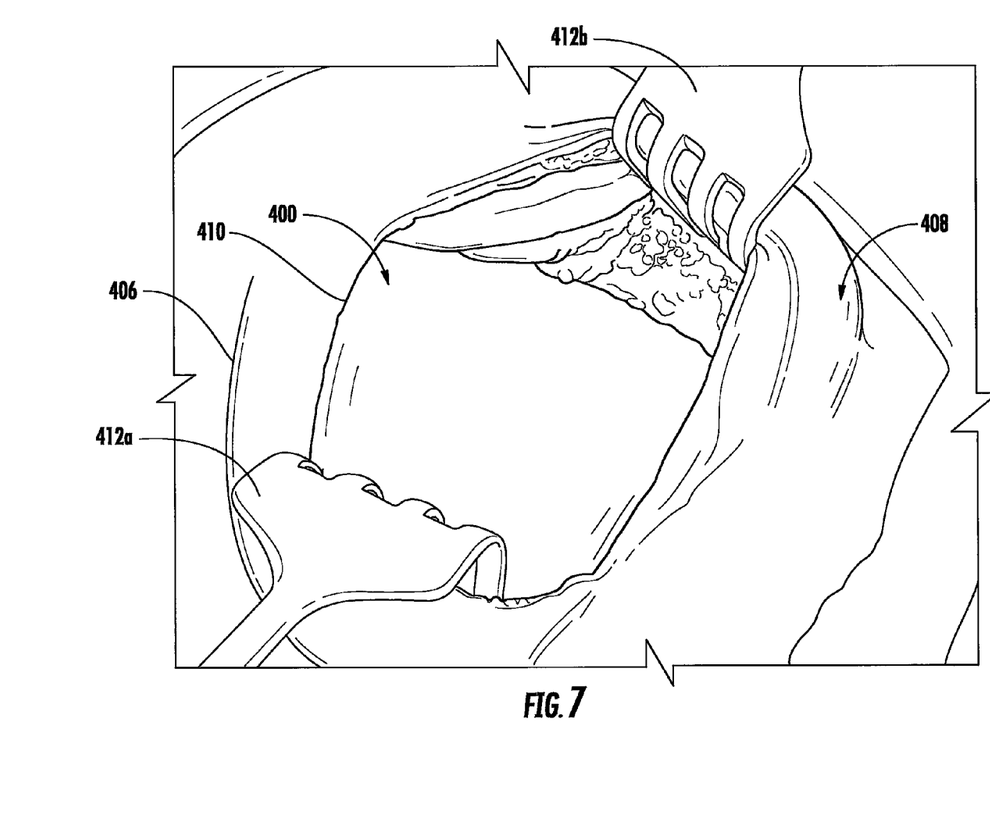
FIG. 7 illustrates a perspective view of the breast implant template of FIG. 6 inserted into the subcutaneous post-mastectomy pocket.
Figure 8:
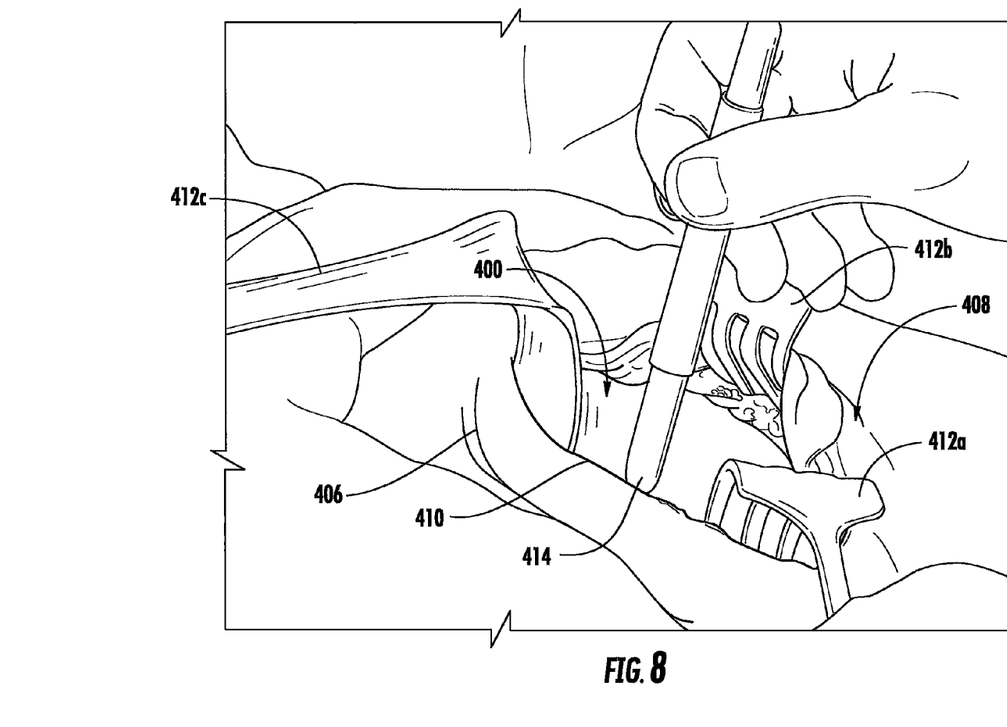
FIG. 8 illustrates a perspective view of marking along a perimeter of the breast implant template of FIG. 6.
Figure 9:
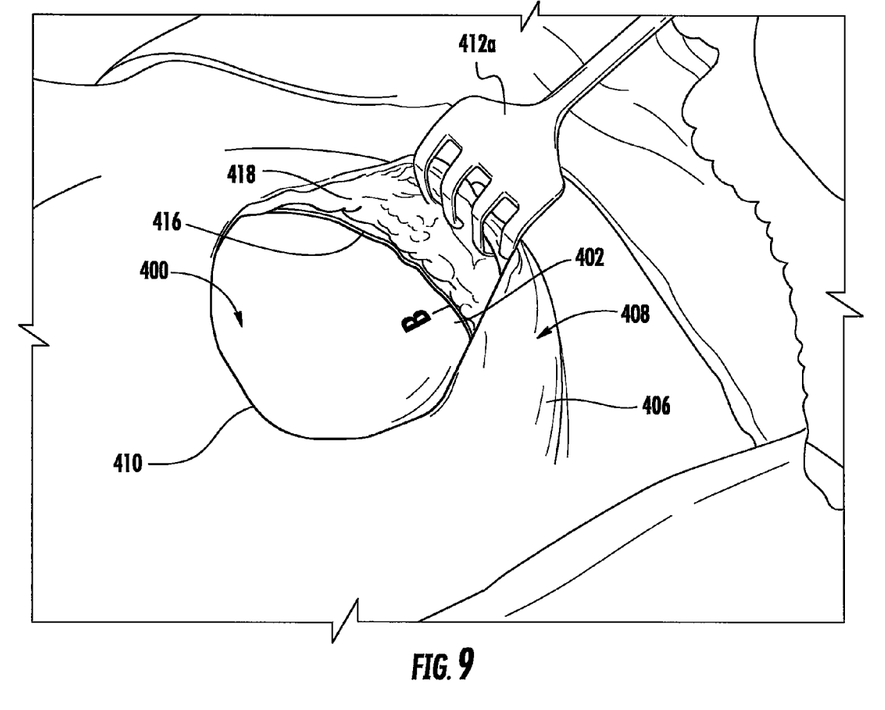
FIG. 9 illustrates a perspective view of a mark on a chest wall created around a perimeter of the breast implant template of FIG. 6.
Figure 10:
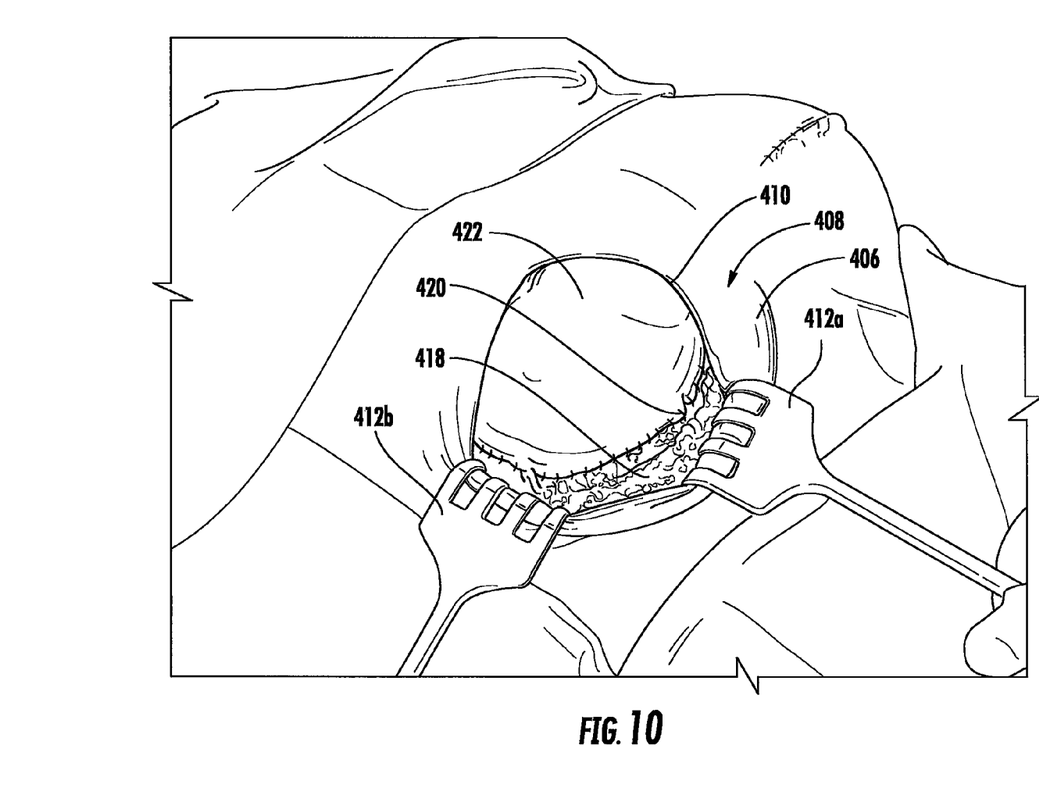
FIG. 10 a perspective view of a fixation suture line between the chest wall and an acellular dermal matrix along the mark illustrated in FIG. 9.

FIG. 6 illustrates the breast implant template 400 positioned over a breast, prior to use thereof. An inframammary fold line 406 is drawn on the chest of the patient at the bottom of the breast. FIG. 7 illustrates the breast 408 after creating an incision therein, which defines an opening 410 when held apart by first and second retractors 412a,b. FIG. 8 illustrates an additional third retractor 412c holding the opening 410 open while a marking tool 414 (e.g., an ink marker or pen) is employed to mark a fixation suture line. More particularly, as illustrated in FIG. 9, in the illustrated embodiment the breast implant template 400 is employed to select a location for a mark 416 along a chest wall 418 of the patient. As illustrated, the location of the mark 416 may be selected by tracing around the perimeter 402 of the breast implant template 400. Accordingly, the breast implant template 400 conveniently allows a surgeon to mark the location for the fixation suture line 420, which is illustrated in FIG. 10, and which couples an ADM 422 to the chest wall 418. Note that the breast implant template 400 may be removed from the breast 408 prior to attaching the acellular dermal matrix 422 to the chest wall 418.

The order in which the ADM is attached to the chest wall, the ADM is attached to the pectoralis muscle, the breast implant template is employed to determine one or more fixation suture lines, and the breast implant is inserted in the breast may vary. However, in one example embodiment, the ADM may first be sutured to a free end of the pectoralis muscle. Then the breast implant template may be employed to select and mark one or more fixation suture lines. The ADM may then be sutured, but untied or not knotted (e.g., by holding the sutures in place with hemostats) to the chest wall. Next, the breast implant may be inserted in the breast beneath the layer created by the pectoralis muscle and the ADM. Finally, the sutures between the ADM and the chest wall may be tied or knotted. However, the order of operations may vary from this example embodiment.

In some embodiments the breast implant template 400 may be provided as part of a breast implant kit comprising the breast implant template and a breast implant and/or an acellular dermal matrix. The breast implant template 400 may also be provided in various sizes and shapes that match the sizes and shapes of a variety of breast implants. Thereby, the breast implant template 400 may be configured to precisely match the size and shape of the breast implants, as described above. In some embodiments the 3-D forms 200 described above may also be provided in the kit.

As illustrated in FIG. 6, in some embodiments the templates 400 may optionally include a handle or tab 424. The tab 424 may be employed by a user to easily remove the template 400 from the breast cavity. For example, in one embodiment the tab 424 may be employed by a cut through the template 400 that defines the shape of the tab. In some embodiments the tab 424 may be centered with respect to the remainder of the form 400 such that when the tab 424 is pulled, the template at least partially folds and defines smaller dimensions facilitating removal from the breast cavity through the opening thereto.

Figure 11:
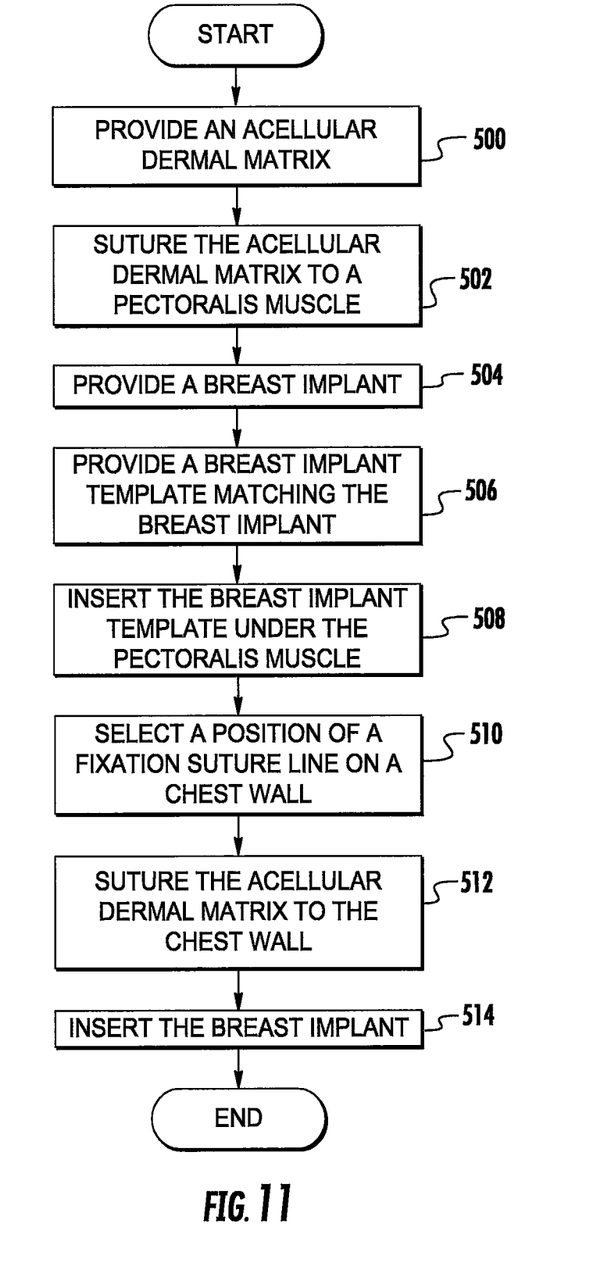
FIG. 11 illustrates a schematic diagram of a surgical method employing a breast implant template according to an example embodiment of the present disclosure.

A related surgical method is also provided. As illustrated in FIG. 4, the method may comprise providing an ADM at operation 500. The method may also include suturing the ADM to a pectoralis muscle of a patient at operation 502. Further, the method may include providing a breast implant defining a perimeter with a shape and one or more dimensions at operation 504 and providing a breast implant template comprising a sheet of a flexible material defining a perimeter with a shape and one or more dimensions substantially matching the shape and the dimensions of the perimeter of the breast implant at operation 506.

Additionally, the method may include inserting the breast implant template under the pectoralis muscle at operation 508 and selecting a position of a fixation suture line on a chest wall of the patient based on a position of the perimeter of the breast implant template at operation 510. The method may further comprise suturing the ADM to the chest wall along the fixation suture line at operation 512. Also, the method may include inserting the breast implant between the pectoralis muscle and the ADM at operation 514.

In some embodiments selecting the position of the fixation suture line at operation 510 may comprise marking the chest wall. The method may additionally include selecting the breast implant template with the shape and the dimensions substantially matching the shape and the dimensions of the perimeter of the breast implant from a plurality of breast implant templates defining at least one of a plurality of shapes and a plurality of sizes. In this regard, the surgeon may be provided with a plurality of breast implants from which to select, and a corresponding plurality of breast implants with matching shapes and sizes.

In some embodiments the 3-D forms, 2-D templates and methods described herein may be employed in direct-to-implant immediate breast reconstructions following mastectomy. For example, the 3-D forms, 2-D templates and methods described herein may be particularly helpful during procedures involving use of an acellular dermal matrix. However, use of the 3-D forms, 2-D templates and methods described herein may also be employed in other implant procedures.

Further, as described above, the 3-D forms and 2-D templates may be provided and shapes configured to match commercially available sizes and shapes of breast implants. In some embodiments the 3-D forms and 2-D templates may be color-coded depending on a size thereof such that the size thereof may be quickly determined. Further, in some embodiments the 3-D forms and 2-D templates may define relatively bright colors (e.g., blaze orange or safety yellow) configured to be visible when the 3-D forms and 2-D templates are received in the breast cavity. Thus, the 3-D forms and 2-D templates may be highly visible which may facilitate the above-described operations. In another embodiment the 3-D forms may be configured to glow or otherwise emit light for the same purpose.

Note also that the 2-D templates and 3-D forms may be configured to be sterile. In this regard, use of the 2-D templates and 3-D forms intra-operatively requires sterility in order to prevent infection in the breast cavity. Sterilization may be accomplished via subjecting the 2-D templates and 3-D forms to one or more processes such as heating in an autoclave. In this regard, as noted above, the material(s) defining the 2-D templates and 3-D forms may be configured to undergo such sterilization processes without suffering material breakdown or other damage.

Although the foregoing disclosure has been described in detail by way of illustration and example for purposes of clarity and understanding, it will be recognized that the above described disclosure may be embodied in numerous other specific variations and embodiments without departing from the spirit or essential characteristics of the disclosure. Certain changes and modifications may be practiced, and it is understood that the disclosure is not to be limited by the foregoing details, but rather is to be defined by the scope of the appended claims.

What is claimed is:

1. A surgical method, comprising:
providing an acellular dermal matrix;
suturing the acellular dermal matrix to a pectoralis muscle of a patient;
providing a breast implant defining a perimeter with a shape and one or more dimensions;
providing a breast implant template comprising a generally flat and planar sheet of a flexible material defining a perimeter with a shape and one or more dimensions substantially matching the shape and the dimensions of the perimeter of the breast implant;
inserting the breast implant template under the pectoralis muscle;
selecting a position of a fixation suture line on a chest wall of the patient based on a position of the perimeter of the breast implant template;
removing the breast implant template from the patient;
suturing the acellular dermal matrix to the chest wall along the fixation suture line after removing the breast implant template from the patient; and
inserting the breast implant between the pectoralis muscle and the chest wall in a pocket defined at least in part by the acellular dermal matrix.

2. The surgical method of claim 1, wherein selecting the position of the fixation suture line comprises marking the chest wall.

3. The surgical method of claim 1, further comprising selecting the breast implant template with the shape and the dimensions substantially matching the shape and the dimensions of the perimeter of the breast implant from a plurality of breast implant templates defining at least one of a plurality of shapes and a plurality of sizes.

* * * * *